United States Patent [19]

Couvreur et al.

[11] Patent Number: 4,913,908

[45] Date of Patent: Apr. 3, 1990

[54] PREPARATION OF SUBMICROSCOPIC PARTICLES, PARTICLES THUS OBTAINED AND PHARMACEUTICAL COMPOSITIONS CONTAINING THEM

[75] Inventors: Patrick Couvreur, Wavre; Michel Roland, Brussels, both of Belgium; Peter Speiser, Forch, Switzerland

[73] Assignee: N. V. Sopar S.A., Sart-Dames-Avelines, Belgium

[21] Appl. No.: 193,139

[22] Filed: May 6, 1988

Related U.S. Application Data

[63] Continuation of Ser. No. 370,892, Apr. 22, 1982, abandoned.

[30] Foreign Application Priority Data

Apr. 24, 1981 [FR] France ............................ 81 08172

[51] Int. Cl.$^4$ ......................... A61K 9/50; A61K 9/18; A61K 9/52
[52] U.S. Cl. .................................. 424/501; 424/1.1; 424/7.1; 424/486; 424/487; 427/213.31; 427/213.34; 428/402.22; 514/965; 526/297
[58] Field of Search ................ 424/1.1, 486, 487, 501; 427/213.31, 213.34; 428/402.22; 526/297

[56] References Cited

U.S. PATENT DOCUMENTS

| | | | |
|---|---|---|---|
| 4,269,821 | 5/1981 | Kreuter et al. | 424/501 |
| 4,329,332 | 5/1982 | Couvreur | 424/9 |
| 4,489,055 | 12/1984 | Couvreur et al. | 424/7.1 |

FOREIGN PATENT DOCUMENTS

| | | |
|---|---|---|
| 809607 | 1/1979 | Belgium . |
| A007895 | 7/1979 | European Pat. Off. . |
| 49-34299 | 9/1974 | Japan ............................ 427/213.34 |

OTHER PUBLICATIONS

Couvreur, P. et al., "Polycyanoacrylate Nanocapsules as Potential Lysosomotropic Carriers: Preparation, Morphological and Sorptive Properties", J. Pharm. Pharmacol. 1979, 31: pp. 331–332.
Chemical Abstracts, vol. 94, No. 12, 3/23/81–Ref. 90245b, p. 409, Int. J. Pharm. 1980, 7(1), 45–53; B. Kante et al, Tissue Distribution of ($^3$H) Actinomycin D Adsorbed on Polybutylcyanoacrylate Nanoparticles.
Chemical Abstracts, vol. 94, No. 10, 3/9/81, Ref. 71390d, p. 372, Eur. J. Cancer 1980, 16(11), F. Brasseur et al; Actinomycin D Adsorbed on Polymethylcyanoacrylate Nanoparticles Increased Efficiency Against an Experimental Tumor.
Chemical Abstracts, vol. 91, No. 22, 11/26/79–Ref. 181375y, p. 387, & J. Pharm. Pharmacol. 1979, 31(5) 331–332 P. Couvreur et al: Polycyanoacrylate Nanocapsules as Potential Lysosomotropic Carriers: Preparation, Morphological and Sorptive Properties.
Chemical Absatracts, vol. 86, No. 10, 3/7/77–ref. 60455n, p–348 & J. Pharm. Pharmacol. 1976, 28(7), 539–543 A. T. Florence et al: Interfacial Properties of Polymethyl Alpha–Cyanoacrylate and Polybutyal Alpha–Cyanoacrylate.
Chemical Abstracts, vol. 83, No. 6, Aug. 11, 1975, ref. 48196j, p. 305 & JP–A–74–34 299 (Tomoegawa Paper Mfg. Co.), 13 Sep. 1974.
Journal of Pharmaceutical Sciences, vol. 68, No. 12, Dec. 1979, P. Couvreur Adsorption of Antineoplastic Drugs to Polyalkylcyanoacrylate Nanoparticles and Their Release in Calf Serum, pp. 1521–1524.
Journal of Pharmaceutical Sciences No. 12, Dec. 1976, vol. 65.
G. Birrenbach et al. Polymerized Micelles and Their Use as Adjuvants in Immunology., pp. 1763–1766.
Chemical Abstracts, vol. 88, No. 24, 12–6/1978, p. 426 Ref. 177057s, J. J. Marty et al, Nanoparticles a New Colloidal Drug Delivery System.
Chemical Abstracts, vol. 89, No. 8, 21–8–1978, p. 334, ref. 65167s J. Kreuter Nanoparticles and Nanocapsules New Dosage Forms in The Nanometer Size Range.

*Primary Examiner*—Richard D. Lovering
*Attorney, Agent, or Firm*—Beveridge, DeGrandi & Weilacher

[57] ABSTRACT

Process for the preparation of submicroscopic particles formed of a polymerized alkyl cyanoacrylate and containing a biologically active substance.

At least one alkyl cyanoacrylate, in which the term "alkyl" denotes an alkyl radical having 1 to 12 carbon atoms, is added, with stirring, to pure water or to an aqueous solution or aqueous colloidal solution of an acid and/or of another water-soluble substance, and the stirring is continued until substantially all the alkyl cyanoacrylate has been converted to submicroscopic particles formed of polyalkyl cyanoacrylate; a biologically active substance is introduced into the reaction medium before the introduction of the monomer or after formation of the submicroscopic particles.

The submicroscopic particles are useful as carriers for substances such as medical substances or products for diagnosis.

29 Claims, No Drawings

PREPARATION OF SUBMICROSCOPIC PARTICLES, PARTICLES THUS OBTAINED AND PHARMACEUTICAL COMPOSITIONS CONTAINING THEM

This application is a continuation of copending application Ser. No. 370,892 filed Apr. 22, 1982, now abandoned.

The present invention relates to a new process for the preparation of submicroscopic particles formed of a polymerized alkyl cyanoacrylate and containing a biologically active substance. The invention also relates to the said submicroscopic particles and to the pharmaceutical compositions in which they are present.

Submicroscopic particles having a diameter of less than 500 nanometers, formed of a cyanoacrylic polymer, are already known from U.S. patent application Ser. No. 057,767, filed on Jul. 16th, 1979, now U.S. Pat. No. 4,329,332, issued May 11, 1982, which describes submicroscopic particles formed by the micellar polymerization of an alkyl cyanoacryalte, in which the term "alkyl" denotes a lower alkyl radical having 1 to 4 carbon atoms, and containng a biologically active substance.

U.S. patent application Ser. No. 057,767, filed on Jul. 16th, 1979, now U.S. Pat. No. 4,329,332, also describes a process for the preparation of these submicroscopic particles. In the process of preparation described in the said patent application, the monomer (alkyl cyanoacrylate) is added, with stirring, to an aqueous solution of a surface-active agent, the pH of which is adjusted to a value of less than 7, and preferably of between 2 and 3, with a pharmacologically acceptable acid. The alkyl cyanoacrylate then polymerizes in the form of submicroscopic particles; the biologically active substance is introduced in the medium either before the introduction of the monomer or after polymerization.

The submicroscopic partiles according to U.S. patent application Ser. No. 057,767, filed on Jul. 16th, 1979, now U.S. Pat. No. 4,329,332, have a number of very valuable properties as carriers for biologically active substances, which ca be, for example, medicinal substances for human or veterinary use or products for diagnosis.

However, these known submicroscopic particles have certain disadvantages which limit their application in medicine.

A first disadvantage of the submicroscopic particles according to U.S. patent application Ser. No. 057,767, filed on Jul. 16th, 1979, now U.S. Pat. No. 4,329,332, results from the process by which they are prepared. In fact, the process for the preparation of these submicroscopic particles, such as described in the said U.S. patent application, involves the use of a surface-active agent.

Now, the presence of surface-active agents in pharmaceutical preparations intended for parenteral administration is not desirable, in particular because of the inherent toxicity of these products.

It is true that the process of preparation described in U.S. patent application Ser. No. 057,767, filed on Jul. 16th, 1979, now U.S. Pat. No. 4,329,332, makes provision, in particular, for the use of non-ionic surface-active agents. The non-ionic surface-active agents which can thus be used are generally less toxic than the ionic surface-active agents, but nevertheless have a certain toxicity which makes their presence in pharmaceutical compositions rather undesirable, especially if these compositions are intended for parenteral administration. It should be noted in this respect that the removal of the surface-active agents, after the preparation of the submicroscopic particles, is a virtually impossible or very difficult operation requiring the use of extremely delicate purification methods (ultra-filtration, ultradialysis and/or ultracentrifugation), which are rather incompatible with industrial-scale manufacture.

It is also important to note that, in certain cases, it is not possible in practice to remove the surface-active agents from the composition without at the same time removing a substantial proportion of the biologically active substance which was absorbed into the submicroscopic particles.

A second disadvantage of the submicroscopic particles according to U.S. patent application Ser. No. 057,767, filed on Jul. 16th, 1979, now U.S. Pat. No. 4,329,332, which also results from the process for their preparation, is the fact that these particles are prepared in a reaction medium of which the pH is adjusted to a value of less than 7 and preferably of between 2 and 3. The presence of an acid in the reaction medium is generally undesirable because, in any case, it will have to be neutralized at the final stage of the preparation of the pharmaceutical composition.

Moreover, the presence of an acid in the reaction medium can be distintly harmful if it is desired to attach, to these submicroscopic particles, a biologically active substance which would be adversely affected or decomposed on contact with an acid.

It is true that, in certain cases, this difficulty could be avoided by preparing the submicroscopic particles in an acid medium and by not adding the biologically active substance until after the pH of the medium has been adjusted to a value close to 7. This procedure, which would avoid adversely affecting the biologically active substance, is not without disadvantage, however, because the amount of biologically active substance which can be attached to the submicroscopic particles is always smaller when the biologically active substance is introduced into the medium after formation of the submicroscopic particles, than when this same substance is introduced into the medium before the introduction of the monomer.

Apart from the two disadvantages mentioned above in respect of the submicroscopic particles according to U.S. patent application Ser. No. 057,767, filed on Jul. 16th, 1979, now U.S. Pat. No. 4,329,332, it must also be noted that these submicroscopic particles, which are obtained by the polymerization of lower alkyl cyanoacrylates, are not suitable for certain applications in medicine because of the fact that they are biodegraded too rapidly in the organism, with the result that they are not suitable as carriers for medicinal substances requiring a slower release.

The present invnetion overcomes the abovementioned disadvantages.

According to the present invention, it has been discovered, surprisingly, that biodegradable submicroscopic particles having a diameter of less than 600 nanometers (containing at least one biologically active substnace) can be prepared by the polymerization of an alkyl cyanoacrylate in an aqueous medium, in the absence of surface-active agents (it being possible for the biologically active substance to be introduced into the reaction medium before the introduction of the monomer or after the formation of the submicroscopic particles). It is important to note here that alkyl cyanacrylates are insoluble in water, and it was therefore totally unexpected that a monomer of this type, added to an aqueous medium to which surface-active agents have not been added, could polymerize to form submicroscopic particles having a diameter of less than 600 nanometers.

According to a particular and generally advantageous embodiment of the present invention, it has also been discovered, surprisingly, that the said biodegradable submicroscopic particles can also be prepared by the polymerization of an alkyl cyanoacrylate in an aqueous medium which is not only free of surface-active agents, but is also free of acid. A process of this type is undoubtedly new and novel, not only because of the absence of surface-active agents in the reaction medium, but also because of the absence of acid. The fact that submicroscopic particles having a diameter of less than 600 nanometers can be prepared by adding an alkyl cyanoacrylate to a non-acid aqueous medium is in fact surprising, because alkyl cyanoacrylates (and in any case lower alkyl cyanoacrylates) are very active monomers, and it was generally acknowledged that, in the absence of acid, they polymerize very rapidly as soon as they come into contact with basic substances or with non-acidified water.

The processes according to the present invention make it possible, in particular, to prepare submicroscopic particles starting from alkyl cyanoacrylates, in which the term "alkyl" denotes a linear or branched alkyl radical having 5 to 12 carbon atoms. These submicroscopic particles are new and advantageous because, in the human or animal organism, they have a slower biodegradation rate than the submicroscopic particles obtained starting from lower alkyl cyanocrylates (with an alkyl radical containing from 1 to 4 carbon atoms), and they are thus very particularly suitable as carriers for medicinal substances requiring a slow and gradual release.

The present invention relates to a process for the preparation of submicroscopic particles having a diameter of less than 600 nanometers, formed of a synthetic polymer and containing at least one biologically active substance, this preparation being carried out in the absence of a surface-active agent.

According to one embodiment of the invention, the process consists in:

preparing an aqueous solution or aqueous colloidal solution of at least one biologically active substance, this aqueous solution or aqueous colloidal solution being free of surface-active agent, adding at least one alkyl cyanoacrylate, in which the term "alkyl" denotes a linear or branched alkyl radical having 1 to 12 carbon atoms, to this aqueous solution or aqueous colloidal solution, with stirring, and continuing the stirring until substantially all the alkyl cyanoacrylate introduced into the reaction medium has been converted to submicroscopic particles formed of polyalkyl cyanoacrylate.

According to another embodiment of the invention, the process consists in:

preparing an aqueous solution or aqueous colloidal solution of at least one biologically active substances and of at least one other substance chosen from amongst salts, sugars, polysaccharides and othe pharmaceutically acceptable water-soluble substances, this aqueous solution or aqueous colloidal solution being free of surface-active agent and having an osmotic pressure similar to the osmotic pressure of blood serum, adding at least one alkyl cyanoacrylate, in which the term "alkyl" denotes a linear or branched alkyl radical having 1 to 12 carbon atoms, to this aqueous solution or aqueous colloidal solution, with stirring, and continuing the stirring until substantially all the alkyl cyanoacrylate introduced into the reaction medium has been converted to submicroscopic particles formed of polyalkyl cyanoacrylate.

According to another embodiment of the invention, the process consists in:

preparing an aqueous solution or aqueous colloidal solution of one or more substances chosen from amongst salts, sugars, polysaccharides and other pharmaceutically acceptable water-soluble substances, this aqueous solution or aqueous colloidal solution being free of surface-active agent and having an osmotic pressure similar to the osmotic pressure of blood serum, adding an alkyl cyanoacrylate, in which the term "alkyl" denotes a linear or branched alkyl radical having 1 to 12 carbon atoms, to this aqueous solution or aqueous colloidal solution, with stirring, continuing the stirring until substantially all the alkyl cyanoacrylate introduced into the reaction medium has been converted to submicroscopic particles formed of polyalkyl cyanoacrylate, and adding an aqueous solution or aqueous colloidal solution of at least one biologically active substance to this suspension of submicroscopic particles.

According to a particular method of carrying out each of the three processes described above, the aqueous solution or aqueous colloidal solution to which the alkyl cyanoacrylate is added is free of acid.

According to another method of carrying out each of these three processes, the said aqueous solution or aqueous colloidal solution is adjusted to a pH of less than 7 with at least one pharmaceutically acceptable acid. More particularly, this pH can be adjusted to a value of between 2 and 3.

According to another embodiment of the invention, the process consists in:

preparing an aqueous solution of at least one pharmaceutically acceptable acid (more particularly, the pH of this solution can be between 2 and 3), adding at least one alkyl cyanoacrylate, in which the term "alkyl" denotes a linear or branched alkyl radical having 1 to 12 carbon atoms, to this aqueous solution, with stirring, continuing the stirring until substantially all the alkyl cyanoacrylate introduced into the reaction medium has been converted to submicroscopic particles formed of polyalkyl cyanoacrylate, and adding an aqueous solution or aqueous colloidal solution of at least one biologically active substance to this suspension of submicroscopic particles.

If, in one or other embodiment of the invention, the alkyl cyanoacrylate is introduced into an acid reaction medium, the suspension of submicroscopic particles formed will advantageously be adjusted to a pH of between 6 and 8 by adding at least one pharmaceutically acceptable basic substance.

According to a particular embodiment of the invention, the process consists in:

adding at least one alkyl cyanoacrylate, in which the term "alkyl" denotes a linear or branched alkyl radical having 6 to 12 carbon atoms, to pure water, with stirring, continuing the stirring until substantially all the alkyl cyanoacrylate introduced into the water has been converted to submicroscopic particles formed of polyalkyl cyanoacrylate, and adding an aqueous solution or aqueous colloidal solution of at least one biologically active substance to this suspenstion of submicroscopic particles.

If, in arder to carry out the invention, the alkyl cyanoacrylate is introduced into an acidified reaction medium, the acid used can be, for example, hydrochloric, hydrobromic, hydriodic, sulfuric, phosphoric, acetic, succinic, lactic or citric acid or any other pharmaceutically acceptable acid, provided that the said acid is compatible with the components of the medium and in particular with the biologically active substance.

The pH of a suspension of submicroscopic particles prepared in an acid medium can be adjusted to a value of between 6 and 8 by adding at least one pharmaceutically acceptable basic substnace such as, for example, a solution of sodium hydroxide or a buffer solution of monopotassium phosphate and sodium hydroxide.

Substances intended for increasing the osmotic pressure, such as, for example, sodium chloride, glucose or dextran, can be added to the reaction medium or to the suspension of submicroscopic particles. These substances can be added after the preparation of the suspension of submicroscopic particles, but if a sugar or a polysaccharide (such as glucose or dextran) is used, it is generally advantageous to introduce this substance into the reaction medium before introducing the alkyl cyanoacrylate therein, because this procedure makes it possible, with certain monomers, to obtain submicroscopic particles having a smaller average diameter.

The submicroscopic particles according to the invention can contain one or more biologically active substances. The biologically active substances which the submicroscopic particles can contain are, for example, medicinal substances for human or veterinary use or products for diagnosis. Medicinal substances which may be mentioned more particularly are chemical products possessing pharmacological properties and, for example, antimitotic or antineoplastic substances, such as methotrexate, actinomycin D, doxorubicin, daunorubicin, bleomycin and vincristine, or antibiotic substances, such as penicillins, cephalosporins and nalidixic acid, antibiotics of the aminoglucoside type and those of the virginiamycin family, or hormonal substances, in particular steroidal hormones. These medicinal substances can be, in particular, high molecular weight chemical compounds, such as insulin and heparin, and the expression "medicinal substances" also includes biological products, such as antigens, allergens, enzymes, proteins, viruses, constituents or viruses, constituents of bacteria or constituents of cells. The submicroscopic particles according to the invention can also contain a product for diagnosis, such as, for example, fluorescein or radioactive human seralbumin.

The present invention also relates, by way of a new industrial product, to the submicroscopic particles having a diameter of less than 400 nanometers, formed by the polymerization of an alkyl cyanoacrylate, in which the term "alkyl" denotes a linear or branched alkyl radical having 5 to 12 carbon atoms and, in particular, the hexyl radical, these particles containing at least one biologically active substance.

The invention also relates to the pharmaceutical compositions of these submicroscopic particles.

The invention also relates to the pharmaceutical compositions which contain submicroscopic particles containing at least one biologically active substance, obtained in accordance with one or other of the processes according to the invention.

The pharmaceutical compositions according to the invention can contain an excipient for oral or parenteral administration.

The invention also relates to the pharmaceutical compositions which consist of an aqueous suspension of submicroscopic particles such as that obtained by one or other of the processes of the invention.

According to an advantageous embodiment of the invention, the pharmaceutical compositions contain submicroscopic particles having an average diameter of less than 200 nanometers and preferably of less than 100 nanometers.

Pharmaceutical compositions of this type are very especially suitable for parenteral administration and more particularly for intravenous administration.

The examples which follow illustrate the present invention without in any way limiting its scope.

It will be noted that Examples 1 to 8 in a way relate to "blank" experiments, since they describe the preparation of submicroscopic particles free of biologically active substance. It will be understood, however, that submicroscopic particles containing a biologically active substance can be prepared analobgously by introducing the said biologically active substance into the reaction medium, either before the introduction of the cyanoacrylate or after the formation of the submicroscopic parttictles, in a manner analogous to that described in Examples 9 to 13.

In all the examples mentioned below, the submicroscopic particles are prepared at ambient temperature (about 20° C.).

It should be noted, furthermore, that, for all the examples mentioned below, the size of the submicroscopic particles was measured with a laser beam diffraction counter (Nanosizer ®). It is important to know that the results of the measurements obtained in this way must be considered to be overestimated compared with the results which would be obtained by particle size analysis using a scaning electron microscope.

EXAMPLE 1

50 microliters of hexyl cyanoacrylate are added to 25 ml of distilled water, with stirring. After a polymerization time of 4 days, 50 microliters of hexyl cyanoacrylate are again added. After a further period of 4 days, 50 microliters of hexyl cyanoacrylate are again added and the polymerization is allowed to continue for a further period of 4 days. It should be noted that the stirring has been maintained from the start of the preparation. The suspension of submicroscopic particles thus obtained exhibits a Tyndall effect characteristic of colloidal solutions. This suspension is filtered on a sintered glass filter (pore diameter: 9 to 15 micrometers). Measured with the aid of a laser beam diffraction counter (Nanosizer ®), the particles contained in the filtrate have an average diameter of 80 nanometers.

EXAMPLE 2

The technique described in Example 1 is followed, but the distilled water is replaced by a 5% strength solution of glucose in order to make the suspension isotonic and hence suitable for injection as such.

The average diameter of the nanoparticles thus obtained is 170 nanometers.

EXAMPLE 3

100 mg of dextran 70 and 200 mg of citric acid are dissolved successively in 10 ml of distilled water. 120 microliters of hexyl cyanoacrylate are then added dropwise. After filtration, particles having an averatge diameter of the order of 300 nanometers are obtained.

EXAMPLE 4

100 mg of citric acid and 100 mg of dextran are dissolved in 10 ml of distilled water. 120 microliters of methyl cyanoacrylate are added dropwise. After a polymerization time of 2 hours, the suspension is filtered on a sintered glass filter (pore diameter: 9 to 15 micrometers). The particles thus obtained have an average diameter of about 600 nanometers.

EXAMPLE 5

The technique described in Example 4 is followed, but the methyl cyanoacrylate is replaced by isobutyl cyanoacrylate. The particles thus obtained have an average diameter of about 450 nanometers.

EXAMPLE 6

500 mg of glucose are dissolved in 10 ml of distilled water. 120 microliters of methyl cyanoacrylate are added dropwise. After a polymerization time of 2 hours, the suspension is filtered on a sintered glass filter (pore diameter: 9 to 15 micrometers). The particles thus obtained have an average diameter of 160 nanometers and the suspension is isotonic and ready for injection.

EXAMPLE 7

The techniques described in Example 6 is followed, but the methyl cyanoacrylate is replaced by ethyl cyanoacrylate. The particles thus obtained have an average diameter of 150 nanometers.

EXAMPLE 8

The technique described in Example 6 is followed, but the methyl cyanoacylate is replaced by isobutyl cyanoacrylate. The particles thus obtained have an average diameter of 180 nanometers.

EXAMPLE 9

100 mg of citric acid and 100 mg of dextran 70 are dissolved in 10 ml of distilled water. 100 microliters of hexyl cyanoacrylate are added dropwise, with stirring, and this stirring is maintained for 4 hours. After neutralization with N NaOH to pH 7, 1 mg of actinomycin D and 5 microliters of a solution of tritiated actinomycin D (specific activity: 14 Ci/millimole; radioactice concentration: 0.5 mCi/ml) are added to the suspension thus obtained. The stirring is continued for 2 hours and the suspension thus obtained is then centrifuged at 50,000 G. By determination of the radioactivity (liquid scintillator) in the supernatant liquid and in the centrifugation residue, it is found that the amount of actinomycin D attached to the submicroscopic particles corresponds to 50.2% of the total amount used.

The average diameter of the particles obtained is 260 nanometers.

EXAMPLE 10

200 mg of citric acid are dissolved in 10 ml of distilled water. 120 microliters of hexy cyanoacrylate are added dropwise, with stirring, and this stirring is maintained for 4 hours. After neutralization with N NaOH to pH 7, 5 mg of vincristine and 50 microliters of a solution of tritiated vincristine (specific activity: 4.5 Ci/millimole; radioactive concentration: 0.25 mCi/ml) are added to the suspension thus obtained. The stirring is continued for 2 hours and the suspension thus obtained is then centrifuged at 50,000 G. By determination of the radioactivity (liquid scintillator) in the supernatant liquid and in the centrifugation residue, it is found that the amount of vincristine attached to the submicroscopic particles corresponds to 69% of the total amount used.

The average diameter of the particles obtained is 150 nanometers.

EXAMPLE 11

200 mg of citric acid are dissolved in 10 ml of distilled water. 120 microliters of hexyl cyanoacrylate are added dropwise, with stirring, and this stirring is maintained for 4 hours. After neutralization with N NaOH to pH 7, 100 I.U. of porcine insulin and 10 microliters of insulin labeled with iodine 125 (specific activity: 50 $\mu$Ci/mg; radioactive concentration: 1 $\mu$Ci/ml) are added to the suspension thus obtained. The stirring is continued for 2 hours and the suspension thus obtained is then centifuged at 50,000 G. By determination of the radioactivity (gamma scintillator) in the supernatant liquid and in the centrifugation residue, it is found that the amount of porcine insulin attached to the submicroscopic particles corresponds to 93% of the total amount used.

The average diameter of the particles obtained is 150 nanometers.

EXAMPLE 12

500 mg of glucose are dissolved in 10 ml of distilled water. Twice 40 microliters of hexyl cyanoacrylate are added, with stirring, at an interval of 4 days. The stirring is maintained until the fourth day after the second addition of monomer. 10 mg of doxorubicin are then added. Under these conditions, and after filtration, particles having an average diameter of 190 nanometers are obtained, to which an amount of doxorubicin of the order of 60% of the total amount used is attached.

EXAMPLE 13

100 mg of dextran 70 and 50 mg of citric acid are dissolved successively in 10 ml of distilled water. 10 mg of $CaCl_2$ are then dissolved in the same medium in order to prevent possible hypocalcemia when the pharmaceutical composition is injected. 10 mg of doxorubicin are then dissolved in the same medium. 100 microliters of isobutyl cyanacrylate are finally added dropwise to the reaction medium, with stirring. After a polymerization time of 4 hours, with stirring, the preparation is buffered to pH 7 with N NaOH and the suspension is made isotonic with 72 mg of NaCl. The preparation is ready for intravenous administration and the particles thus obtained have an average diameter of 140 nanometers.

After centrifugation of the ultrafine suspension at 50,000 G and fluorimetric determination of the doxorubicin in the supernatant liquid and in the centrifugation residue, it is found that the amount of doxorubicin attached to the particles corresponds to 94% of the total amount used.

Several toxicity measurements are carried out with suspensions of particles obtained by this process. Irrespective of the method of administration, the inherent toxicity of doxorubicin is substantially reduced when it is absorbed by the submicroscopic particles.

Thus, for example, after intravenous adminsitration of three successive doses of 10 mg/kg/day of free doxorubicin, 27.5% of the mice do not survive for 15 days. On the other hand, when the same amount of doxorubicin attached to submicroscopic particles is administered to mice, no mortality is recorded after 15 days.

Likewise, none of the mice survives three injections of 12.5 mg/kg/day of free doxorubicin, whereas, when this medicament is attached to submicroscopic particles and administered at the same doses, 30% of the mice survive.

Parallel to this, the weight loss of mice treated with doxocrubicin attached to submicroscopic particles is substantially smaller than the weight loss of mice treated with free doxorubicin.

The inherent toxicity of doxorubicin greatly limits the doses which can be administered and hence the therapeutic efficacy. The experiments described above show that the attachment of this cytostatic medicament to submicroscopic particles according to the invention reduces its toxicity, which thus makes it possible to increase the doses and hence the therapeutic effect of the medicament.

We claim:

1. A process for the preparation of an aqueous suspension of submicroscopic particles having a diameter of less than 600 nanometers, formed of a biodegradable synthetic polymer and containing at least one biologically active substance adsorbed into and/or attached to the polymer carrier particles, which comprises:
    preparing an aqueous solution or aqueous colloidal solution of at least one biologically active substance, this asqueous solution or aqueous colloidal solution being free of surface-active agent,
    adding a polymer forming composition consisting of at least one alkyl cyanoacrylate, in which the term "alkyl" denotes a linear or branched alkyl radical having 1 12 carbon atoms, to this aqueous solution or aqueous colloidal solution, with stirring, and
    continuing the stirring until substantially all the alkyl cyanoacrylate introduced into the aqueous reaction medium has been converted to submicroscopic particles formed of polyalkyl cyanoacrylate, the entire process being carried out without a surfactant.

2. A process as claimed in claim 1, wherein the aqueous solution or aqueous colloidal solution to which the alkyl cyanoacrylate is added is free of acid.

3. A process as claimed in claim 1, wherein before the alkyl cyanacrylate is added thereto, the said aqueous solution or aqueous colloidal solution is adjusted to a pH of less than 7 with at least one pharmaceutically acceptable acid.

4. A process for the preparation of an aqueous suspension of submicroscopic particles having a diameter of less than 600 nanometers, formed of a biodegradable synthetic polymer and containing at least one biologically active substance adsorbed into and/or attached to the polymer carrier particles, which comprises:
    preparing an aqueous solution or aqueous colloidal solution of at least one biologically active substance and of least one other substance selected from the group consisting of salts, sugars, polysaccharides and other pharmaceutically acceptable water-soluble substances, this aqueous solution or aqueous colloidal solution being free of surface-active agent and having an osmotic pressure similar to the osmotic pressure of blood serum,
    adding a polymer forming composition consisting of at least one alkyl cyanoacrylate, in which the term "alkyl" denotes a linear or branched alkyl radical having 1 to 12 carbon atoms, to this aqueous solution or aqueous colloidal solution, with stirring, and
    continuing the stirring until substantially all the alkyl cyanoacrylate introduced into the aqueous reaction medium has been converted to submicroscopic particles formed of polyalkyl cyanoacrylate, the entire process being carried out without a surfactant.

5. Submicroscopic particles containing at least one biologically active substance in an aqueous suspension obtained by a process as claimed in claim 1.

6. A pharmaceutical composition which contains submicroscopic particles as claimed in claim 5 and an excipient for oral or parenteral administration.

7. A process as claimed in claim 3, wherein after the formation of the suspension of submicroscopic particles, the pH of this suspension is adjusted to a value of between 6 and 8 by adding at least one pharmaceutically acceptable basic substance.

8. A process as claimed in claim 7, wherein the aqueous solution or aqueous colloidal solution to which the alkyl cyanoacrylate is added is free of acid.

9. A process as claimed in claim 7, wherein before the alkyl cyanoacrylate is added thereto, the said aqueous solution or aqueous colloidal solution is adjusted to a pH of less than 7 with at least one pharmaceutically acceptable acid.

10. A process as claimed in claim 9, wherein after the formation of the suspension of submicroscopic particles, the pH of this suspension is adjusted to a value of between 6 and 8 by adding at least one pharmaceutically acceptable basic substance.

11. Submicroscopic particles containing at least one biologically active substance in an aqueous suspension obtained by a process as claimed in claim 7.

12. A pharmaceutical composition which contains submicroscopic particles as claimed in claim 11 and an excipient for oral or parenteral administration.

13. Process for the preparation of an aqueous suspension of submicroscopic particles having a diameter of less than 600 nanometers, formed of a biodegradably synthetic polymer and containing at least one biologically active substance adsorbed into and/or attached to the polymer carrier particles, which comprises:
    preparing an aqueous solution or aqueous colloidal solution of at least one substance selected from the group consisting of salts, sugars, polysaccharides and other pharmaceutically acceptable water-soluble substances, this aqueous solution or aqueous colloidal solution being free of surface-active agent and having an osmotic pressure similar to the osmotic pressure of blood serum,
    adding a polymer forming composition consisting of at least one alkyl cyanoacrylate, in which the term "alkyl" denotes a linear or branched alkyl radical having 1 to 12 carbon atoms, to this aqueous solution or aqueous colloidal solution, with stirring,
    continuing the stirring until substantially all the alkyl cyanoacrylate introduced into the aqueous reaction medium has been converted to submicroscopic particles formed of polyalkyl cyanoacrylate, and
    adding an aqueous solution or aqueous colloidal solution of at least one biologically active substance to this suspension of submicroscopic particles, the entire process being carried out without a surfactant.

14. A process as claimed in claim 13, wherein the aqueous solution or aqueous colloidal solution to which the alkyl cyanoacrylate is added is free of acid.

15. A process as claimed in claim 13, wherein before the alkyl cyanoacrylate is added thereto, the said aqueous solution or aqueous colloidal solution is adjusted to a pH of less than 7 with at least one pharmaceutically acceptable acid.

16. A process as claimed in claim 15, wherein after the formation of the suspension of submicroscopic particles, the pH of this suspension is adjusted to a value of between 6 and 8 by adding at least one pharmaceutically acceptable basic substance.

17. Submiscroscopic particles containing at least one biologically active substance in an aqueous suspension obtained by a process as claimed in claim 13.

18. A pharmaceutical composition which contains submicroscopic particles as claimed in claim 17 and an excipient for oral or parenteral administration.

19. A process for the preparation of an aqueous suspension of submicroscopic particles having a diameter of less than 600 nanometers, formed of a biodegradable synthetic polymer and containing at least one biologically active substance adsorbed into and/or attached to the polymer carrier particles, which comprises:
preparing an aqueous solution of at least one pharmaceutically acceptable acid, wherein the aqueous solution is free of surface-active agent,
adding a polymer forming composition consisting of at least one alkyl cyanoacrylate, in which the term "alkyl" denotes a linear of branched alkyl radical having 1 to 12 carbon atoms, to this aqueous solution, with stirring,
continuing the stirring until substantially all the alkyl cyanoacrylate introduced into the aqueous reaction medium has been converted to submicroscopic particles formed of polyalkyl cyanoacrylate, and
adding an aqueous solution or aqueous colloidal solution of at least one biologically active substance to this suspension of submicroscopic particles, the entire process being carried out without a surfactant.

20. A process as claimed in claim 19, wherein after the formation of the suspension of submicroscopic particles, the pH of this suspension is adjusted to a value of between 6 and 8 by adding at least one pharmaceutically acceptable basic substance.

21. Submicroscopic particles containing at least one biologically active substance in an aqueous suspension obtained by a process as claimed in claim 19.

22. A pharmaceutical composition which contains submicroscopic particles as claimed in claim 21 and an excipient for oral or parenteral administration.

23. A process for the preparation of an aqueous suspension of submicroscopic particles having a diameter of less than 600 nanometers, formed of a biodegradable synthetic polymer and containing at least one biologically active substance adsorbed into and/or attached to the polymer carrier particles, which comprises:
adding at least one alkyl cyanoacrylate, in which the term "alkyl" denotes a linear or branched alkyl radical having 6 to 12 carbon atoms, to pure water in the absence of surface-active agent, with stirring,
continuing the stirring until substantially all the alkyl cyanoacrylate introduced into the water has been converted to submicroscopic particles formed of polyalkyl cyanoacrylate, and
adding an aqueous solution or aqueous colloidal solution of at least one biologically active substance to this suspension of submicroscopic particles, the entire process being carried out without a surfactant.

24. Submicroscopic particles containing at least one biologically active substance in an aqueous suspension obtained by a process as claimed in claim 23.

25. A pharmaceutical composition which contains submicroscopic particles as claimed in claim 24, and an excipient for oral or parenteral administration.

26. Submicroscopic particles having a diameter of less than 400 nanometers, formed by the polymerization of an alkyl cyanoacrylate in aqueous medium in the absence of surface-active agent, in which the term "alkyl" denotes a linear or branched radical having 6 to 12 carbon atoms, the polymer formed being biodegradable and containing at least one biologically active substance adsorbed into and/or attached to the polymer carrier particles in the aqueous medium, the entire process being carried out without a surfactant.

27. A pharmaceutical composition which contains particles as claimed in claim 26.

28. Particles as claimed in claim 26 having a diameter of less than 200 nanometers.

29. Particles as claimed in claim 26 having a diameter of less than 100 nanometers.

* * * * *